United States Patent
Schmitt

(10) Patent No.: US 7,406,155 B2
(45) Date of Patent: Jul. 29, 2008

(54) X-RAY DEVICE

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 449 days.

(21) Appl. No.: 11/149,383

(22) Filed: Jun. 8, 2005

(65) Prior Publication Data

US 2005/0281378 A1    Dec. 22, 2005

(30) Foreign Application Priority Data

Jun. 8, 2004    (DE) ....................... 10 2004 027 852

(51) Int. Cl.
*H05G 1/54*    (2006.01)

(52) U.S. Cl. ........................ 378/117; 378/114

(58) Field of Classification Search ................. 378/114, 378/115, 116, 117

See application file for complete search history.

(56) References Cited

U.S. PATENT DOCUMENTS

| | | | | |
|---|---|---|---|---|
| 5,844,516 | A * | 12/1998 | Viljanen | ..................... 341/173 |
| 6,409,381 | B1 * | 6/2002 | Siebenhaar et al. | ......... 378/197 |
| 6,476,712 | B1 * | 11/2002 | Achterholt | .................. 340/447 |
| 6,859,521 | B2 | 2/2005 | Spahn | |
| 2004/0008129 | A1 * | 1/2004 | Philipp | ....................... 341/22 |
| 2006/0165371 | A1 | 7/2006 | Zwart | |

FOREIGN PATENT DOCUMENTS

| | | |
|---|---|---|
| DE | 10216857 A1 | 11/2003 |
| WO | 2004036527 A1 | 4/2004 |

* cited by examiner

*Primary Examiner*—Chih-Cheng G Kao

(57) ABSTRACT

X-ray device with at least one switch for triggering a signal and at least one receiver for the signal are provided. The receiver may be arranged remote from the switch. The switch (6) includes an energy converter for converting the mechanical energy expended in the event of the switch being triggered into electrical energy. The signal can then be wirelessly transmitted to the receiver (15) by way of a radio link.

12 Claims, 2 Drawing Sheets

X-RAY DEVICE

CROSS REFERENCE TO RELATED APPLICATIONS

This application claims priority to the German application No. 10 2004 027 852.0, filed Jun. 8, 2004 which is incorporated by reference herein in its entirety.

FIELD OF INVENTION

The invention relates to an x-ray device with at least one switch to trigger a signal and at least one receiver for the signal, said receiver being arranged remote from the switch.

SUMMARY OF INVENTION

Conventional x-ray devices consist of several components spatially separated from one another such as a patient support table, an x-ray emitter ceiling stand and/or an x-ray emitter floor stand as well as a wall stand, which contains a scattered radiation grid and a detector. In addition, an imaging station is usually provided, on which the x-ray programs are selected and the recorded x-ray images can be processed. All components of the x -ray device are connected to one another via electrical lines. Additional control lines are necessary since the user is able to control the x-ray device not only via the imaging station but also on the ceiling stand via the switches. The x-ray device furthermore comprises a series of sensors and end switches, the signals of which must be routed via lines to a central control unit. The numerous implemented operating functions have resulted in the need for several kilometers of cable for the cabling of an x-ray device. One disadvantage here is that the cabling outlay is high, thereby resulting in considerable costs.

It is therefore an object of the invention to specify an x-ray device whereby the cabling outlay is reduced.

This object is achieved by the claims.

In contrast to the x-ray devices known in the prior art, in which the signal is routed to the signal receiver via an electrical cable, provision is inventively made for the switch and the signal receiver to wirelessly communicate with one another. In this way, a considerable portion of the cabling used with conventional x-ray devices is saved, thereby resulting in corresponding cost advantages. A further particularly large advantage is that the switch obtains the energy required for the signal transmission from the switch triggering. In addition, the switch has an energy converter which for example converts the mechanical energy expended in the event of the switch being triggered into electrical energy.

According to a particularly expedient development of the invention, it can be provided that the switch can be triggered by means of a manual activation. In this way, the switch can be coupled with an enter key or a keyboard or a complete operating panel, so that key activations are transmitted wirelessly to the receiver.

According to an alternative embodiment of the invention, it can also be provided that the switch can be triggered in a non-contact manner. The switch can be a proximity switch for example, which signals that a specific position has been reached, a final position for instance. A switch of this type can react for example to magnetic field changes. Non-contact triggerable switches can be used as end switches for a Bucky tray of a mounting stand or a patient support table. It is also possible to transmit specific positions, for example a "zero position" of the moveable Bucky tray in a wireless manner by means of the switch signal.

It is particularly advantageous if the switch comprises a high-frequency transmitter and the receiver comprises a high-frequency receiver. In addition, the switch can comprise a processor for signal preprocessing and the receiver a processor for signal evaluation. Signal preprocessing enables the transmission of complex data, in addition to the simple information such as "0" or "1". In this way, the signal can be configured as a digital radiogram, comprising a more extensive information content.

The x-ray device according to the invention can comprise a plurality of switches and one or more receivers. If each switch and each receiver are assigned a clear identifier, the transmitted signals can simply be assigned to the respective receiver. In this way, a receiver is also able to receive the signals of several switches.

According to an aspect of the invention, it can be provided that the switch comprises a sensor to detect a measurement variable or the switch may be coupled to a separate sensor, and, in either case, the sensor signal can be transmitted to the receiver via the radio link, if necessary after signal preprocessing. By way of example, position or location information of moveable components in the x-ray device can be transmitted in this manner to a central controller.

An x-ray device according to the invention can be particularly easily implemented if the signal can be transmitted via a useable frequency needing no approval. In this case, no separate official inspection or authorization is necessary.

BRIEF DESCRIPTION OF THE DRAWINGS

Further advantages and details of the invention are described with reference to preferred exemplary embodiments in relation to the figures. The figures are schematic representations, in which.

DETAILED DESCRIPTION OF INVENTION

Figure 1:
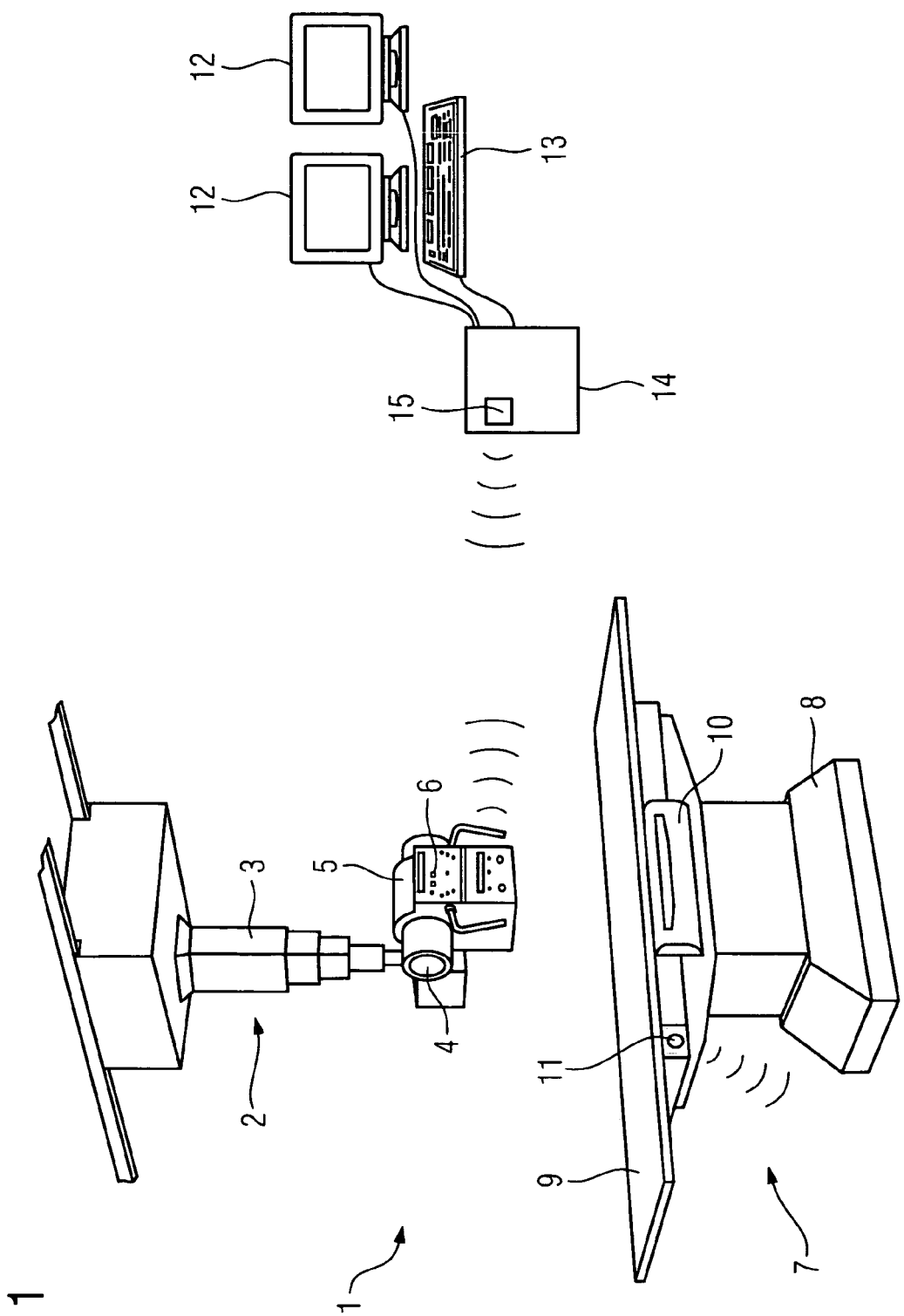
FIG. 1 shows an x-ray device according to a first exemplary embodiment of the invention with a patient support table and a ceiling stand.

The x-ray device 1 shown in FIG. 1 essentially consists of a ceiling stand with an x-ray emitter 4 arranged on a telescopic arm 3. The housing 5 of the x-ray emitter 4 comprises a series of enter keys 6, by means of which the operation of the x-ray device 1 can be controlled. A specific tomographic program can be selected for example via the enter keys 6; the activation of another key can alter the fulcrum height. Similarly, the height of the patient table 7 can be adjusted. By activating an enter key 6 or a switch, the mechanical energy expended with this activation is converted into electrical energy by means of an energy converter. The switch or an enter key 6 comprises a high-frequency transmitter, which transmits the signal entered by the user to a receiver via a radio link. Each transmitter and the receiver has a clear identifier, thereby ensuring that the information is received by the intended recipient.

A collimator is located below the x-ray emitter 4, the light of which is switched on by activating a switch. The switch signal is transmitted from the collimator to a receiver in a similar manner by a radio link.

An SRD radio band (Short Range Device) is used for the radio transmission. In the exemplary embodiment shown, communication takes place at a frequency of 868 MHz. In addition to the identifier of the transmitter, the transmitted radiograms contain several hundred bits of digital information. The radio link enables the transmission of both a single switching pulse and also a measured variable. This may relate to the position of a moveable component in the x-ray device 1 or a measured electrical variable such as a resistance, a current or a voltage.

The patient table 7 consists of a foot 8 and table top 9 which can be moved on three axes in relation to the foot 8 in order to support a patient. A Bucky tray 10 is located below the table top, and can be moved in the longitudinal direction of the table top 9. The movement path of the tray 10 is bordered on both sides by stops. End switches 11 are located at these positions, said end switches being coupled to a transmitter and transmitting a radio signal if the tray is located in the end position.

The patient table 7 has further switches (not shown in FIG. 1), by means of which the brakes are released.

FIG. 1 further shows a schematic representation of an imaging station comprising a display 12 and a keyboard 13, which are connected to a control and computing device 14. A receiver 15 is located in the control and computing device 14, and receives the radio signals sent by the transmitter arranged within the housing 5 and the end switches 11. The receiver 15 has a processor for signal evaluation, so that the control and computing device 14 can control the x-ray device 1 as a function of the received signals.

If the switch to switch on the light of the collimator was activated, a corresponding radio signal is transmitted to the receiver 15. This information reaches the control and computing device 14, which thereupon switches on the current supply for the illumination of the collimator.

Figure 2:
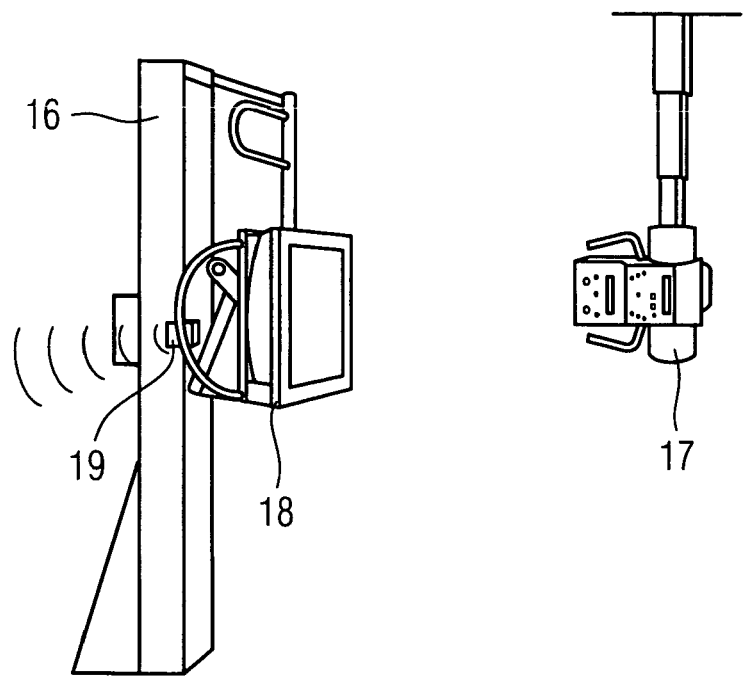
FIG. 2 shows an x-ray device according to a second exemplary embodiment of the invention with a wall stand.

FIG. 2 shows an x-ray device, comprising a wall stand 16 and a ceiling stand 17. The ceiling stand 17 is of the same design as the ceiling stand 2. A Bucky tray 18 can be moved vertically along the wall stand 16. In the case of a specific established height, the Bucky tray 18 is located in the "zero position". A radio signal is triggered in this position, by means of a sensor 19 shown schematically, said sensor operating as a switch. This radio signal is received and evaluated by the receiver 15 of the control and computing device 14.

Figure 3:
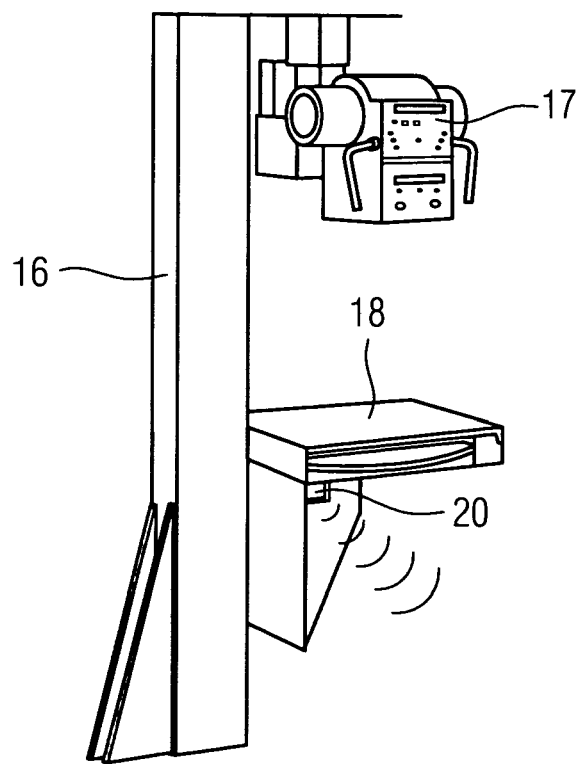
FIG. 3 shows the x-ray device as shown in FIG. 2 with a tilted Bucky tray.

FIG. 3 shows the x-ray device shown in FIG. 2 with a tilted Bucky tray 18. If the tray 18 is positioned horizontally as shown in FIG. 3, the servo tracking can be switched on, whereby the ceiling stand 17 follows the vertical lift of the tray 18. The sensor 20 arranged on the tray 18, which functions as a switch, detects the tilting of the tray 18. If the tray 18 is positioned horizontally, a radio signal is sent to the receiver 15 via a transmitter coupled to the sensor 20. The control and computing device 14 then triggers the servo tracking, so that the wall stand 17 automatically follows the lift movement of the tray 18.

The x-ray device 1 further comprises a cableless remote control, by means of which different operating processes can be triggered. The activation of the push buttons of the remote control causes the mechanical energy to be used to generate the corresponding radio signals.

The invention claimed is:

1. An X-ray device including at least one movable component, comprising:
   at least one mechanically actuatable switch for generating at least one signal, wherein the mechanically actuatable switch includes a first sensor for acquiring a measurement of a parameter indicative of a position of the movable component of the X-ray device, and the signal is a first sensor signal generated by the first sensor;
   at least one receiver arranged remotely relative to the switch, the receiver configured to receive the signal generated by the switch;
   an energy converter included in the switch for converting mechanical energy used to actuate the switch into electrical energy; and
   at least one transmitter for wirelessly transmitting the signal to the receiver using the electrical energy.

2. The X-ray device according to claim 1, wherein the switch is configured to be actuated manually.

3. The X-ray device according to claim 1, wherein the switch is configured to be actuated contactlessly.

4. The X-ray device according to claim 3, wherein the switch is a proximity switch or a magnetic field switch.

5. The X-ray device according to claim 1, wherein the transmitter is included in the switch.

6. The X-ray device according to claim 5, wherein the transmitter is a high-frequency transmitter, and the receiver includes a high-frequency receiver.

7. The X-ray device according to claim 1, wherein the switch includes a first processor adapted for signal preprocessing, and the receiver includes a second processor adapted for signal evaluation.

8. The X-ray device according to claim 1, wherein the X-ray device comprises a plurality of mechanically actuatable switches.

9. The X-ray device according to claim 1, wherein a unique identifier is assigned to each mechanically actuatable switch and each receiver.

10. The X-ray device according to claim 1, wherein the signal is a digital radiogram configured to include pieces of information.

11. The X-ray device according to claim 1, wherein the mechanically actuatable switch is configured to be connected to a second sensor for acquiring a quantity to be measured, and the signal is a second sensor signal generated by the second sensor.

12. The X-ray device according to claim 1, wherein the wireless transmission is executed on a wireless communication channel using a predefined frequency.

* * * * *